(12) United States Patent
Baker (10) Patent No.: US 6,689,129 B2
(45) Date of Patent: Feb. 10, 2004

(54) RF ELECTRODE ARRAY FOR LOW-RATE COLLAGEN SHRINKAGE IN CAPSULAR SHIFT PROCEDURES AND METHODS OF USE

(76) Inventor: James A Baker, 4292-P Wilkie Way, Palo Alto, CA (US) 94306

( * ) Notice: Subject to any disclaimer, the term of this patent is extended or adjusted under 35 U.S.C. 154(b) by 0 days.

(21) Appl. No.: 10/141,273

(22) Filed: May 8, 2002

(65) Prior Publication Data

US 2002/0133214 A1 Sep. 19, 2002

Related U.S. Application Data

(63) Continuation of application No. 09/750,548, filed on Dec. 28, 2000, now abandoned, which is a continuation of application No. 09/257,359, filed on Feb. 25, 1999, now Pat. No. 6,169,926.
(60) Provisional application No. 60/076,199, filed on Feb. 27, 1998.

(51) Int. Cl.[7] ............................................... A61B 18/18
(52) U.S. Cl. .......................... 606/41; 606/47; 606/50; 607/101
(58) Field of Search ................... 606/41, 46, 47, 606/48, 50–51; 607/152, 122, 100, 101, 99

(56) References Cited

U.S. PATENT DOCUMENTS

| | | |
|---|---|---|
| 5,269,780 A | 12/1993 | Roos |
| 5,290,287 A | 3/1994 | Boebel et al. |
| 5,443,463 A | 8/1995 | Stern et al. |
| 5,458,596 A | 10/1995 | Lax et al. |
| 5,697,927 A | 12/1997 | Imran et al. |
| 5,702,390 A | 12/1997 | Austin et al. |
| H1745 H | 8/1998 | Paraschac |
| 5,833,690 A | 11/1998 | Yates et al. |
| 6,001,093 A | 12/1999 | Swanson et al. |
| 6,035,238 A | 3/2000 | Ingle et al. |
| 6,073,052 A | 6/2000 | Zelickson et al. |
| 6,169,926 B1 | 1/2001 | Baker |

Primary Examiner—Linda C. M. Dvorak
(74) Attorney, Agent, or Firm—Ryan Kromholz & Manion, S.C.

(57) ABSTRACT

Methods and apparatus are provided for an achieving low-rate collagen shrinkage using an electrode array comprising an elongated insulator strip having at least one pair of spaced-apart bi-polar RF electrodes, and a "channeling" disposed on the strip between the bi-polar electrodes to direct the flow of RF current therebetween. The channeling electrode is not directly coupled to the RF power source, but only indirectly through the tissue in contact with the channeling electrode. The apparatus enables low RF power levels (e.g., 0.5 watts to 25 watts) to be applied over time intervals of 5 seconds to 180 seconds to attain low-rate collagen shrinkage by directing or focusing the path of the RF current.

11 Claims, 12 Drawing Sheets

RF ELECTRODE ARRAY FOR LOW-RATE COLLAGEN SHRINKAGE IN CAPSULAR SHIFT PROCEDURES AND METHODS OF USE

REFERENCE TO RELATED APPLICATIONS

This application is a continuation of application Ser. No. 09/750,548 filed Dec. 28, 2000, now abandoned which is a continuation of application Ser. No. 09/257,359 filed Feb. 25, 1999 (now U.S. Pat. No. 6,169,926).

This application claims priority from U.S. provisional patent application Ser. No. 60/076,199, filed Feb. 27, 1998.

FIELD OF THE INVENTION

This invention relates to RF (radiofrequency) devices and methods for delivering RF energy to tissue in a patient's body, and more particularly to an electrode array that allows for controlled low-power RF energy delivery in orthopedic applications, for example in capsular shift procedures.

BACKGROUND OF THE INVENTION

Joint instability in adults is caused by ligaments and cartridge in a joint becoming lax or stretched, due either to the aging process or to acute trauma. Joint instability is a widespread disease and is estimated to affect up to 10 percent of the male population in the U.S. A patient's shoulder joints, knees, ankles and elbows all may become unstable due to lax ligaments. As a specific example, a patient's shoulder joint (or glenohumeral joint capsule) is maintained in a stable condition by a capsular ligament complex, subscapular tendons, rotator cuff and teres minor muscles, among others.

Joint instability is caused by laxity in the fibrous ligament complex within the joint capsule. An increase in ligament laxity may be due to an acute-event type of trauma or recurrent minor trauma (i.e., wear-and-tear). Often, acute-event trauma results in a unidirectional type of instability, whereas normal wear-and-tear results in multidirectional joint instability. In terms of pathology, unidirectional joint instability may be defined as an excess capsular volume (space between the humeral head and synovial surface of the capsule) in a particular location, region or path across the capsule. Multi-directional joint instability generally may be considered to be excessive volume within the entire joint capsule around the humeral head.

Surgeons have developed open surgical treatments for reducing the volume of unstable joint capsules, generally termed "capsular shift procedures". In such surgery, over-stretched or lax capsular ligaments are tightened and secured around the perimeter of the joint capsule. Such procedures frequently result in post-operative pain, loss of motion, nerve injury and even osteoarthritis. Further, capsular shift patients require lengthy post-operative rehabilitation and often do not achieve pre-injury levels of joint stability.

Surgeons also have developed minimally invasive arthroscopic techniques for performing capsular shift procedures which, for the most part, replicate the open procedures. An arthroscopic approach typically results in less post-operative pain and reduced rehabilitation time. However, arthroscopic capsular shift techniques require high levels of technical expertise. Also, it is not clear whether arthroscopic ligament fixation devices and methods are equal to those available in an open surgical approach.

More recently, to avoid surgical reconstruction of a joint capsule, arthroscopic surgeons have investigated the use of thermal energy to tighten or shrink the ligaments within a joint capsule. A capsular ligament complex includes various types of collagen, which is one of the most abundant proteins in the human body. It is well-known that collagen fibrils will shrink in length when subjected to temperatures ranging above about 60° C. Interstitial collagen consists of a continuous helical molecule made up of three polypeptide coil chains. Each of the three chains is approximately equal in longitudinal dimension with the molecule, being about 1.4 nm in diameter and 300 nm in length along its longitudinal axis in the helical domain portion.

Collagen molecules polymerize into chains in a head-to-tail arrangement generally with each adjacent chain overlapping another by about one-fourth the length of the helical domain. The spatial arrangement of the three peptide chains is unique to collagen, with each chain existing as a right-handed helical coil. The superstructure of the molecule is represented by the three chains that are twisted into a left-handed superhelix. The helical structure of each collagen molecule is bonded together by heat labile cross-links between the three peptide chains providing the molecule with unique physical properties, including high tensile strength and limited longitudinal elasticity.

The heat labile cross-links may be broken by thermal effects, thus causing the helical structure of the molecule to be destroyed (or denatured) with the peptide chains separating into individually randomly coiled structures of significantly lesser length. The thermal cleaving of such cross-links may result in contraction or shrinkage of the collagen molecule along its longitudinal axis by as much as one-third of its original dimension. It is such thermal shrinkage of collagenous ligament tissue that can stabilize a joint capsule.

Collagen shrinks within a specific temperature range, (e.g., 60° C. to 70° C. depending on its type), which range has been variously defined as: the temperature at which a helical structure collagen molecule is denatured; the temperature at which ½ of the helical superstructure is lost; or the temperature at which the collagen shrinkage is greatest. In fact, the concept of a single collagen shrinkage temperature is less than meaningful, because shrinkage or denaturation of collagen depends not only on an actual peak temperature but on a temperature increase profile (increase in temperature at a particular rate and maintenance at a particular temperature over a period of time).

Thus, collagen shrinkage can be attained through high-energy exposure (energy density) for a very short period of time to attain "instantaneous" collagen shrinkage—the method used by all previously known devices (both laser and high-energy RF waves) for joint capsule shrinkage. These previously known treatments shrink collagenous tissue in a matter of seconds (e.g., 1–2 seconds).

Previously known methods of "instantaneous" capsular collagen shrinkage with a high energy (40 to 60 watts) mono-polar RF probe (or similar high-energy laser) suffer from several significant drawbacks. In such an RF treatment (or laser treatment), the surgeon "paints" the tip of the RF probe across a section of a joint capsule targeted for collagen shrinkage. Because the collagen targeted for shrinkage generally lies well under the capsular surface, high RF energy levels are needed to cause shrinkage, typically 40 to 60 watts. These power levels, however, pose a substantial risk of ablating or perforating the synovial surface, which is highly undesirable.

Figure 1A:
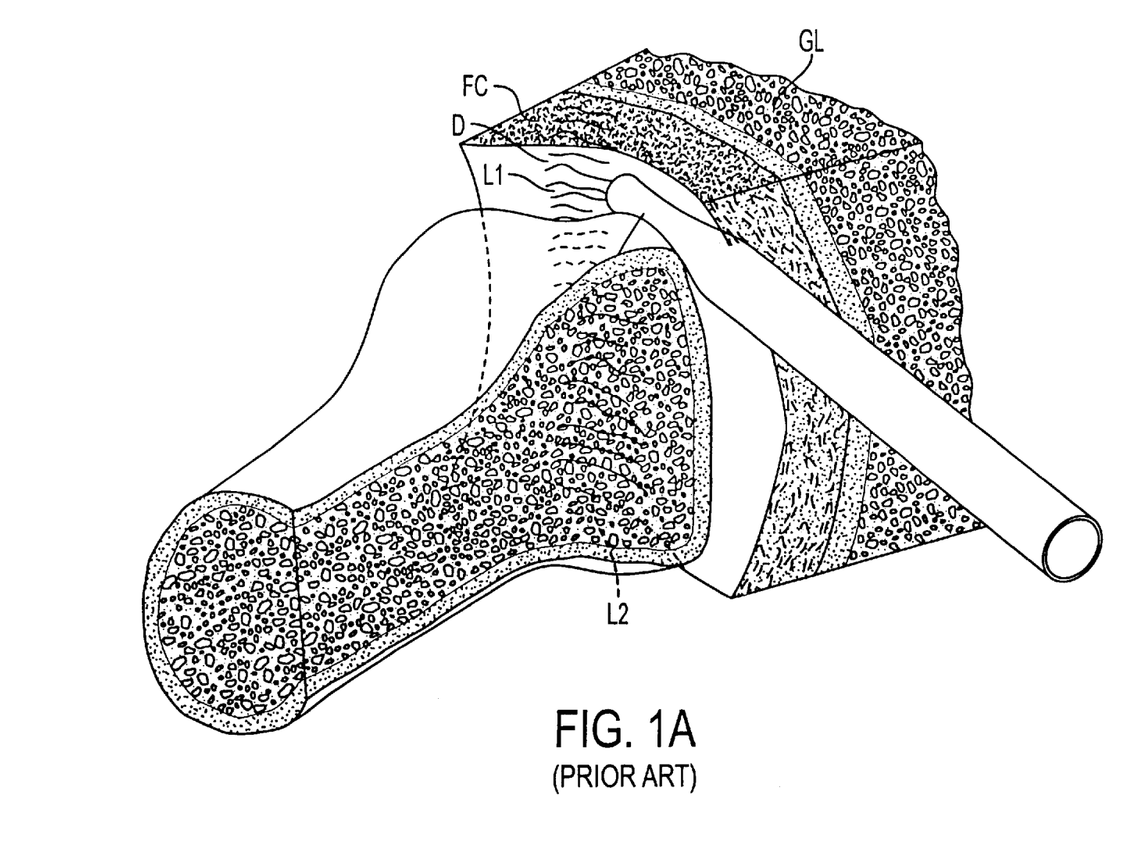
FIGS. 1A–1C are schematic views showing use of a previously known probe to deliver RF energy to a glenohumeral joint to provide rapid collagen shrinkage.

Also, as depicted in FIG. 1A, it is difficult to "paint" the RF probe tip (even though only 3–5 mm in diameter) across the targeted portion of the joint capsule due to the limited working space between humeral head H and capsule C, while still maintaining an adequate endoscopic view of the damaged or lax tissue indicated at D in FIG. 1A. At times, it may be necessary to use an lever-type instrument to pry (or retract) the humeral head away from the joint capsule to provide a larger working space, thus posing a risk of damaging the labrum (the fibrous cartilage surrounding glenoid capsule G).

Further, the previously known methods of creating "instantaneous" collagen shrinkage cause the working space between the humeral head and capsular surface to shrink and disappear practically instantaneously, thus making it necessary to work from a first position treatment location L1 toward a second location L2. Thus, it is generally not possible to return toward the first location L1 for additional treatment or diagnosis (see FIG. 1A).

Previously known methods of "painting" tissue with high-energy RF waves with a hand-held probe to achieve rapid collagen shrinkage are not well suited for collagenous tissues of different thicknesses and/or for tissue in which collagen content varies. For example, the capsular regions carrying the medial and inferior glenohumeral ligaments have significant collagen content (e.g., >85%) and are quite thick. Areas between the ligaments and around the axillary recess are quite thin. Other areas of the joint capsule contain much less collagen (e.g., <40%).

Thus, "painting" the synovial surface with RF waves—even if the probe is moved at a steady rate—will not cause uniform capsular shrinkage. Such free-hand techniques are technically demanding with a steep learning curve. In practice, an experienced surgeon will "paint" the RF probe tip across the capsular surface in high collagen areas, but will stop and hold the probe tip in firm contact with thicker ligament areas (or areas with lesser collagen), in order to apply sufficient heat to the tissue. Such start-and-stop motions, however, tend to pose a risk of ablating and perforating the synovial lining.

Moreover, there are disadvantages in using a hand-held mono-polar RF probe when relying on a thermal sensor in the probe tip to safeguard against surface tissue ablation. While thermal sensors are often touted as having the ability to cut off RF delivery when tissue exceeds a certain temperature, this is generally the case only when a tissue mass is firmly in contact with the sensor. In the above-described "painting" techniques, however, the probe tip contacts the tissue with varying pressures, so that the "actual" tissue temperature may vary greatly from the temperature detected by the probe. Again, there is a substantial risk that the synovial surface may be ablated or perforated by excessively high temperatures before RF current flow is terminated.

Figure 1B:
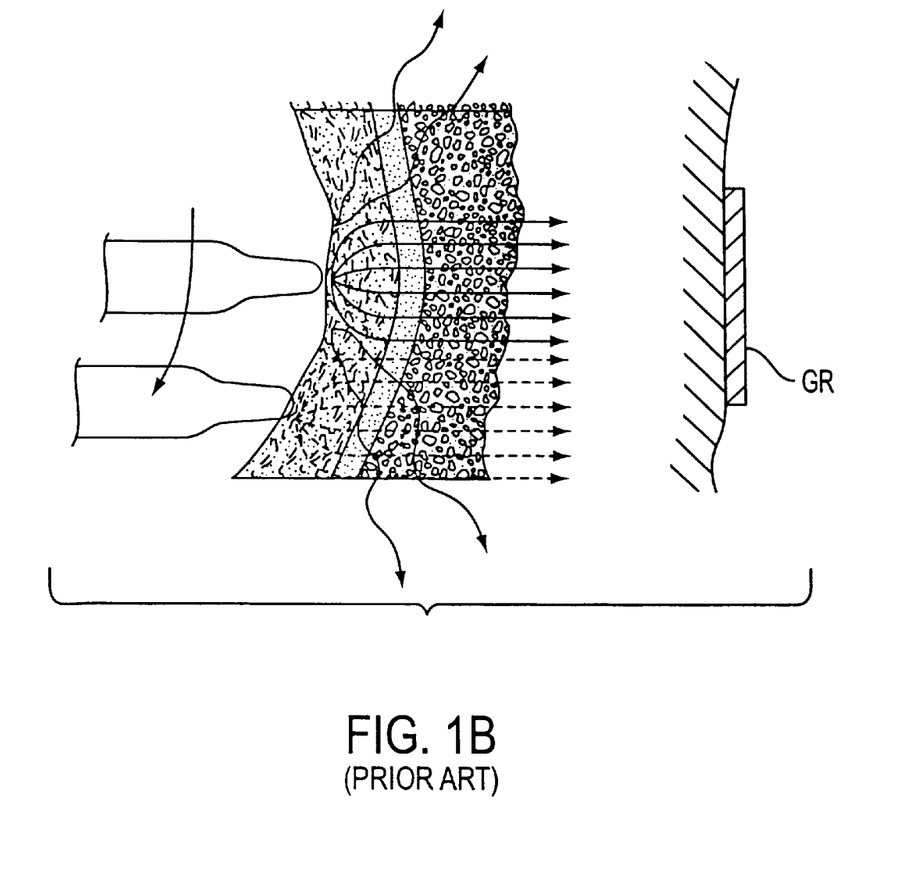

Still other disadvantages of the previously known apparatus and methods are associated with high-energy mono-polar RF delivery. RF energy causes thermal effects in a tissue mass by perturbation or agitation of ions as alternating RF energy courses through the tissue in random paths of least resistance between the active mono-polar RF electrode and a ground plate. As depicted in FIG. 1B, "painting" a mono-polar RF probe tip across a synovial surface causes the RF paths through tissue (to the ground plate) to change constantly, preventing the perturbation of ions in any particular path or location and thus preventing effective energy densities from being attained in any particular location.

Figure 1C:
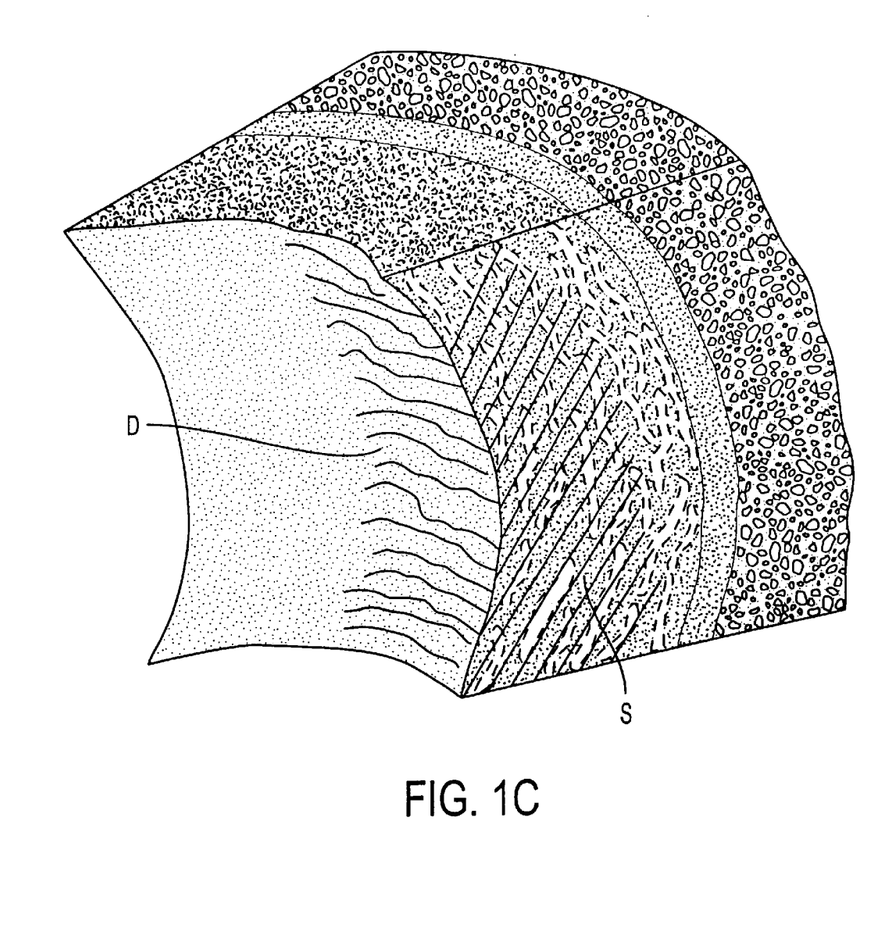

Previously known methods thus achieve "instantaneous" collagen shrinkage only by using a very high current intensity (for high energy densities) that are compatible with the moving electrode ("painting") technique. As shown in FIG. 1B, the RF current paths are only momentarily in a given position and not focused on the tissue that is targeted for ionic agitation. Ideally, as shown in FIG. 1C, the portion of capsular ligaments (depthwise) that need to be heated is indicated by the shaded area.

Yet another disadvantage of previously known mono-polar RF probes relates to the focus of RF energy created around the probe tip. The small diameter of the probe tip (e.g., from 2 mm to 5 mm for reaching into the joint capsule) when energized at high power levels causes the a focus of RF energy at the probe tip. Again, such small diameter mono-polar RF electrodes require much higher energy levels than would be required of a larger electrode to achieve a given level of thermal effects in the joint capsule.

In view of the foregoing, it would be desirable to provide apparatus and methods for elevating the temperature of collagen tissue in a joint capsule that preferably (i) utilize relatively low RF power levels to prevent surface ablation, (ii) are adaptable for treating tissues having high and low collagen content, and (iii) allow for observation of the shrinkage at less than an instantaneous rate.

It also would be desirable to provide apparatus and methods that shrink collagen at lower rates and at a lower temperatures than obtained with previously known RF apparatus and methods.

It further would be desirable to provide apparatus and methods that create a uniform or predictable path for RF current flow through targeted tissue, thereby causing more uniform heating of tissue to a low-rate collagen shrinkage temperature.

SUMMARY OF THE INVENTION

In view of the foregoing, it is an object of this invention to provide apparatus and methods for elevating the temperature of collagen tissue in a joint capsule that preferably (i) utilize relatively low RF power levels to prevent surface ablation, (ii) are adaptable for treating tissues having high and low collagen content, and (iii) allow for observation of the shrinkage at less than an instantaneous rate.

It also an object of the present invention to provide apparatus and methods that shrink collagen at lower rates and at a lower temperatures than obtained with previously known RF apparatus and methods.

It is a further object of this invention to provide apparatus and methods that create a uniform or predictable path for RF current flow through targeted tissue, thereby causing more uniform heating of tissue to a low-rate collagen shrinkage temperature.

These and other objects of the present invention are accomplished by providing an electrode array comprising an elongated insulator strip having at least one pair of spaced-apart bi-polar RF electrodes, and a "channeling" electrode disposed on the strip between the bi-polar electrodes to direct the flow of RF current therebetween. The channeling electrode is not directly coupled to the RF power source, but coupled only indirectly through the tissue in contact with the channeling electrode. The apparatus enables low RF power levels (e.g., 0.5 watts to 25 watts) to be used to attain low-rate collagen shrinkage by directing or focusing the path of the RF current.

In a preferred embodiment, bi-polar electrodes are provided in first and second groups at each end of an elongated insulator strip adapted to be inserted into a joint capsule through a cannula. The bi-polar electrodes are exposed on one surface of the strip, and are connected to a suitable RF source by individual current-carrying wires. Any pair of bi-polar electrodes of the first and second groups may be selected to deliver RF energy. A channeling electrode is disposed on a central portion of the insulator strip, spaced apart from the bi-polar electrodes, with one surface exposed in the same direction as the active electrodes. The channeling electrode has no direct electrical connection to the RF source or any of the active electrodes.

Methods of using the apparatus of the present invention to perform capsular shift procedures are also provided.

BRIEF DESCRIPTION OF THE DRAWINGS

Additional objects and advantages of the invention will be apparent from the following description, the accompanying drawings and the appended claims, in which:

DETAILED DESCRIPTION OF THE INVENTION

The present invention provides apparatus and methods for performing capsular shift procedures, and other similar procedures, using low levels of directed RF power (e.g., between about 0.5 watts to 25.0 watts) to remodel collagen at low shrinkage rates, i.e., where collagenous ligament tissue is elevated to shrinkage temperatures slowly to achieve uniform shrinkage over a large tissue mass. In the preferred embodiment, high frequency alternating RF current (e.g., from 55,000 Hz to 540,000 Hz) is directed between paired bi-polar electrodes, and through a targeted collagenous tissue volume, by a non-energized "channeling electrode" interposed between the bi-polar electrodes.

Alternating RF current causes ionic perturbation and friction within the targeted tissue volume, elevating the tissue temperature as ions follow the changes in direction of the alternating current. Such ionic perturbation thus does not result from direct tissue contact with a resistive electrode that conducts heat into tissue. In the delivery of such RF energy to a soft tissue mass, I=E/R, where I is the intensity of the current in amperes, E is the energy potential measured in volts and R is the tissue resistance measured in ohms. In a soft tissue target, current density (or level of current intensity) is an important gauge of energy delivery, which further relates to the impedance of the target tissue mass.

The level of thermal effects generated within a target tissue volume is influenced by several factors, such as (i) RF current intensity, (ii) RF current frequency, (iii) impedance levels of tissue between paired electrodes, (iv) heat dissipation from the target tissue volume; (v) duration of RF delivery, and (vi) distance through the targeted tissue volume between the paired bi-polar electrodes.

In a preferred embodiment, the apparatus of the present invention comprises an elongate flexible insulator strip having dimensions suitable for introducing the strip into a joint capsule through a cannula. The insulator strip has first and second groups of bi-polar electrodes at each end disposed facing one surface of the strip, each bi-polar electrode facing being coupled to an RF source. A (non-active) channeling electrode is disposed in a central portion of the insulator strip, spaced apart from the bi-polar electrodes, and facing the same surface of the strip as the bi-polar electrodes. The electrode array permits delivery of sufficient RF energy to subsurface tissue to shrink collagen at a low rate, while reducing the risk of desiccating or ablating surface tissues.

Figure 2:
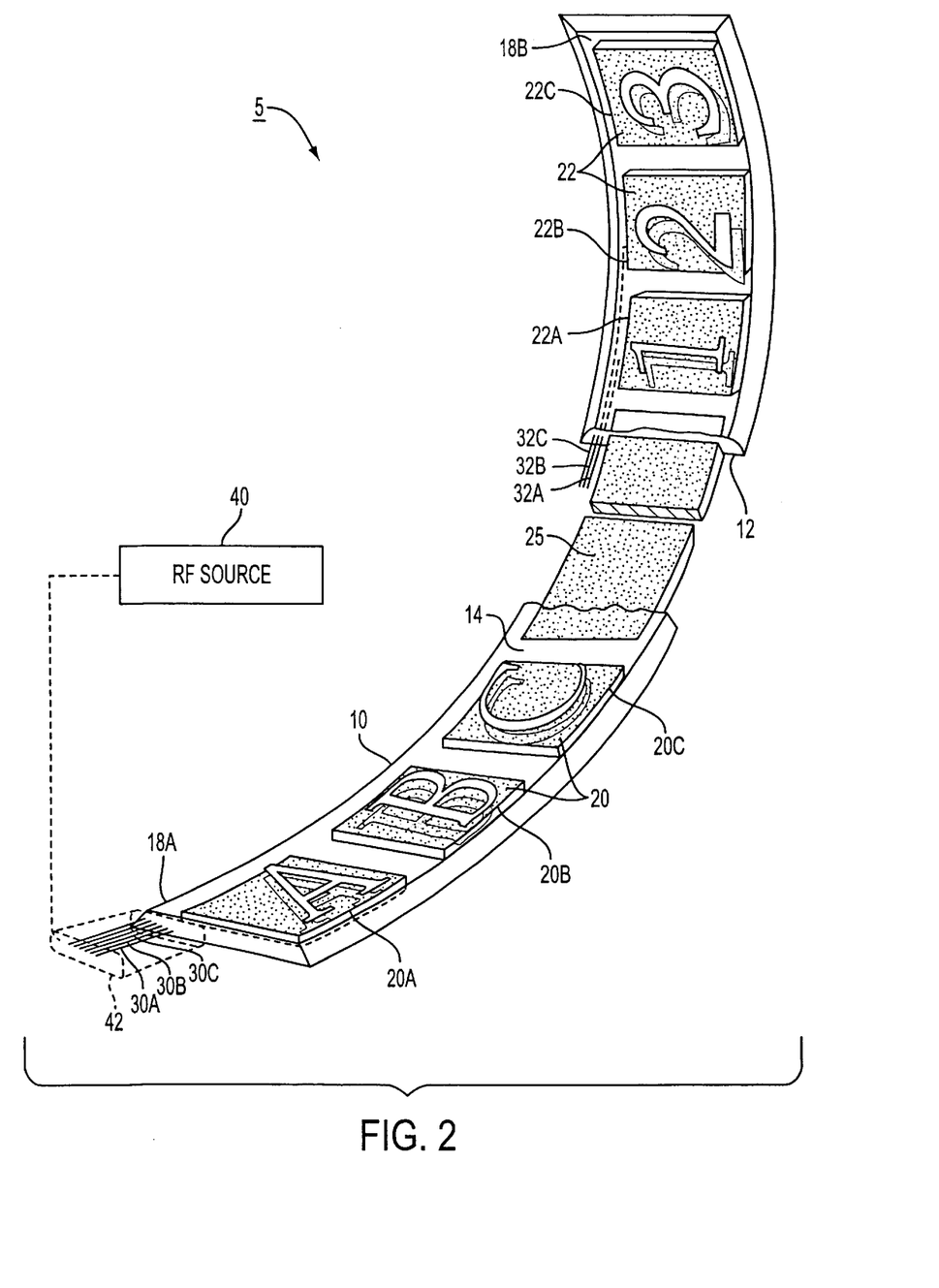
FIGS. 2 and 3 are perspective views of an illustrative embodiment of apparatus of the present invention.
Figure 3:
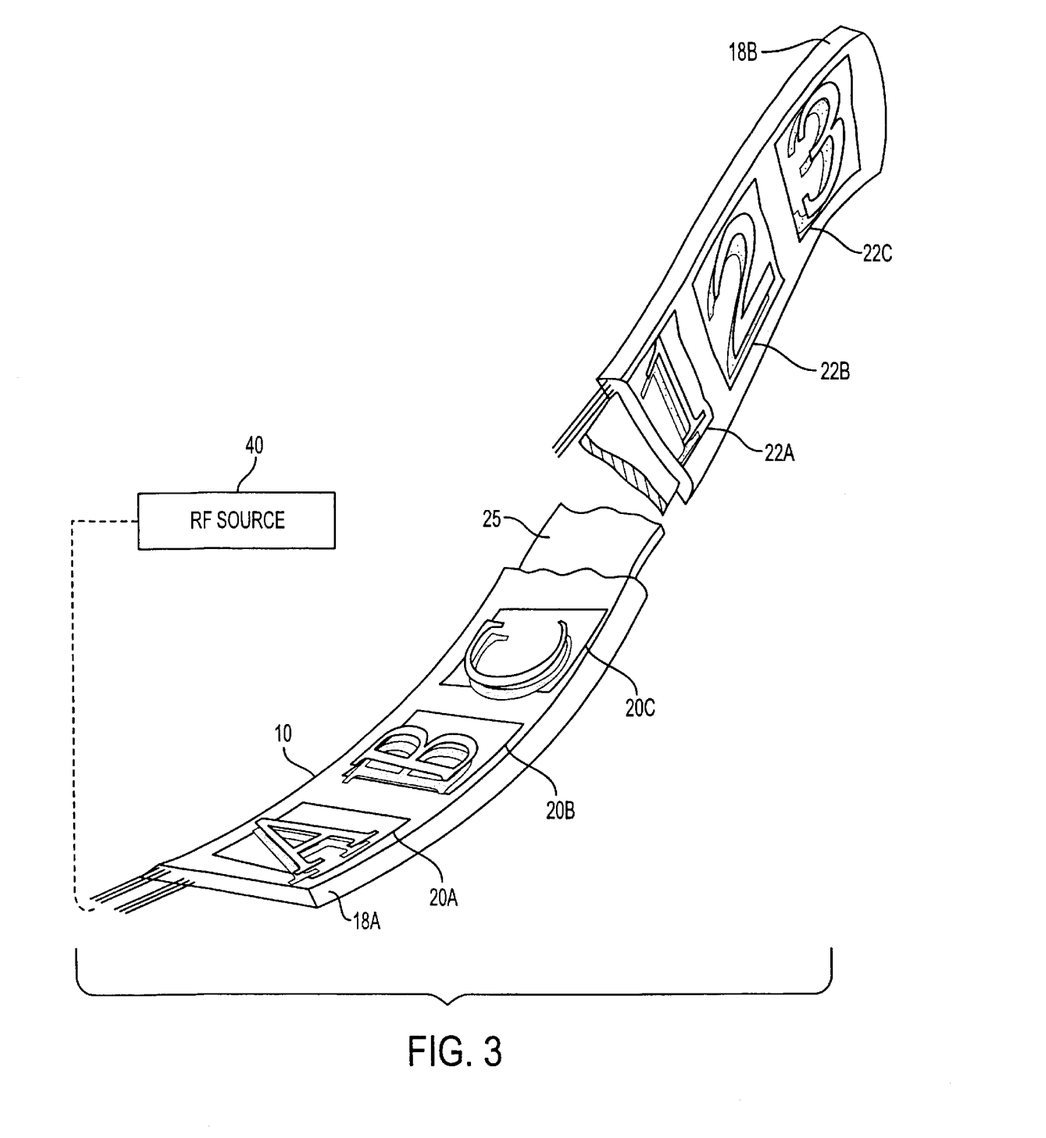

Referring now to FIGS. 2–3, apparatus constructed in accordance with the principles of the present invention is described. Electrode array 5 illustratively is adapted for thermal treatment of a patient's joint capsule, for example a glenohumeral capsule. Electrode array 5 comprises elongated member 10 carrying bipolar electrode groups 20 and 22 and channeling electrode 25. Electrodes groups 20 and 22 and channeling electrode 25 have a lower surface exposed on surface 12 of elongated member 10.

Elongated member 10 preferably is formed from a flexible non-conductive material, such as any suitable medical grade plastic (e.g., vinyl), and includes insulating surface 14 that covers the upper surfaces of all of the electrodes. More preferably, the elongated member 10 comprises a transparent, or substantially transparent, material as shown in FIG. 2. Elongated member 10 preferably has dimensions that allow it to be introduced into a joint capsule through a trocar sleeve or any minimally invasive incision.

In a preferred embodiment, elongated member 10 has a generally rectangular cross-section having and has a thickness as thin as practicable for an intended application. For example; for performing a capsular shift procedure in a glenohumeral joint capsule, elongated member 10 preferably has thickness in a range from 0.5 mm to 3 mm, a width ranging from about 2 mm to 8 mm, and a length in a range from about 30 mm to 80 mm. As shown in FIG. 3, elongated member 10 preferably is sufficiently flexible to twist about its longitudinal axis. In addition, elongated member 10 may comprise a resilient material capable of being springably formed to either a repose curved or linear configuration.

Bi-polar electrode groups 20 and 22 are provided in paired bi-polar groups at left end 18A and right end 18B of elongated member 10. Left-end bi-polar electrode group 20 comprises individual electrodes 20A, 20B and 20C; right-end bi-polar electrode group 22 comprises individual electrodes 22A, 22B and 22C. Electrodes 20A–20C and 22A–22C may be fabricated from a suitable electrically conductive material, for example, gold, nickel titanium, platinum, aluminum or copper, and are embedded in first surface 12 of elongated member 10, for example, during a molding process.

Figure 4:
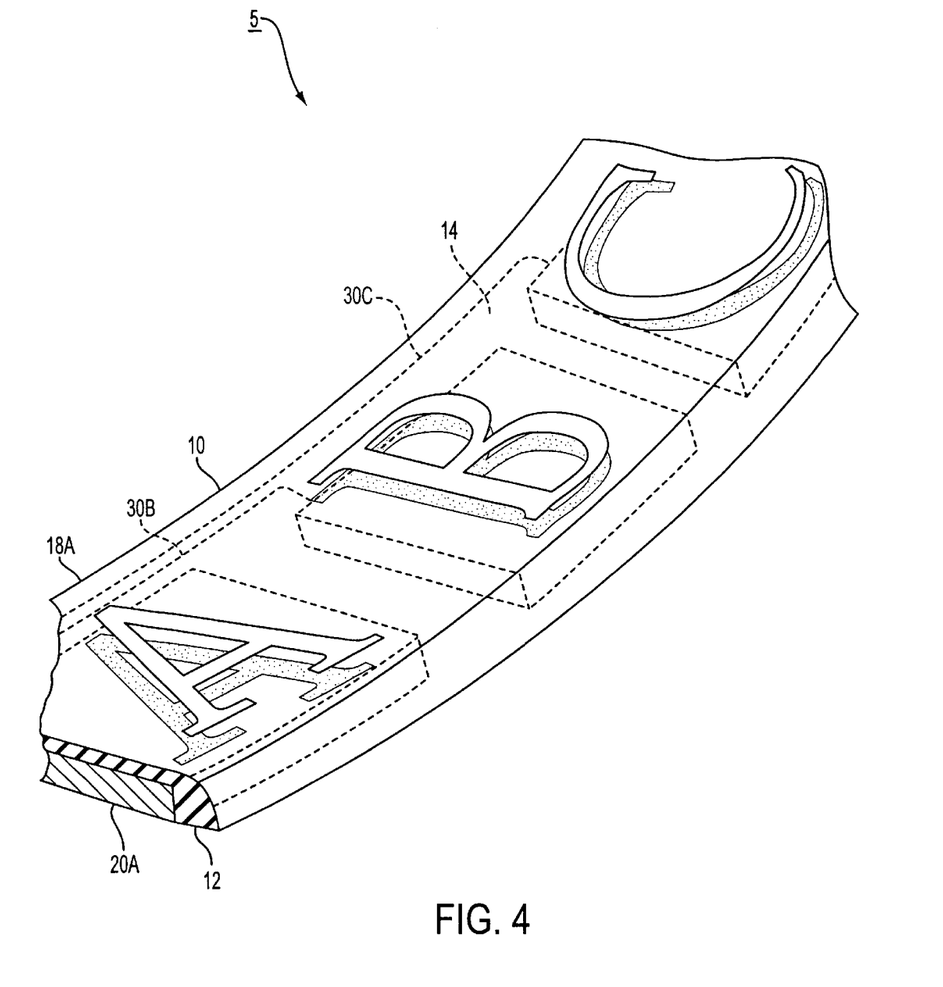
FIG. 4 is an enlarged perspective view one end of the apparatus of FIGS. 2 and 3.

Each bi-polar electrode (20A–20C, and 22A–22C) is connected to RF source 40 by individual current-carrying wires 30A–30C and 32A–32C, respectively (see also FIG. 4). Accordingly, a pair of bi-polar electrodes consisting of any of electrodes 20A–20C paired with any of electrodes 22a–22C may be energized, as described in greater detail below. Current carrying wires 30A–30C and 32A–32C preferably are encased in an insulated cord 42 to permit coupling of the bi-polar electrodes to RF source 40.

In accordance with the principles of the present invention, channeling electrode 25 is disposed with its lower surface exposed on surface 12 of elongated member 10 at a position intermediate left-end group of electrodes 20 and right-end group of electrodes 22. Channeling electrode 25 is not coupled to RF source 40, and is insulated and spaced apart from the "active" bi-polar electrodes. In accordance with the present invention, channeling electrode 25 directs the flow of RF current through the tissue in contact therewith and between the selected pair of bi-polar electrodes 20 and 22.

Channeling electrode 25 may comprise any suitable electrically conductive material, as described above for electrode groups 20 and 22. As will of course be understood, channeling electrode may comprise multiple discrete elements. Alternatively, channeling electrode may extend into and overlap the region carrying bi-polar electrode groups 20 and 22 (e.g., channeling electrode may take the form of rails disposed outwardly of electrode groups 20 and 22 along the width of elongated member 10, and may extend for the length of the elongated member).

Still referring to FIGS. 2 and 3, elongated member 10 has impressed in upper surface 12 a series visual indicator marks A, B, C, and 1, 2, 3, one mark corresponding to each of bi-polar electrodes 20A–20C and 22A–22C, respectively. The visual indicator marks may be any suitable figures or symbols and provide cues that the surgeon can view intra-operatively to determine which two bi-polar electrodes to energize for a given procedure. Indicator marks A-C and 1–3 preferably are as large as possible for easy identification during an arthroscopic procedure. The surgeon may therefore select a particular pair of bi-polar electrodes for activation depending on which electrodes best span an area targeted for treatment. For example, RF current may flow from electrode 20A to 22A, from 20A to 22C, from 20C to 22C, etc.

Figure 5:
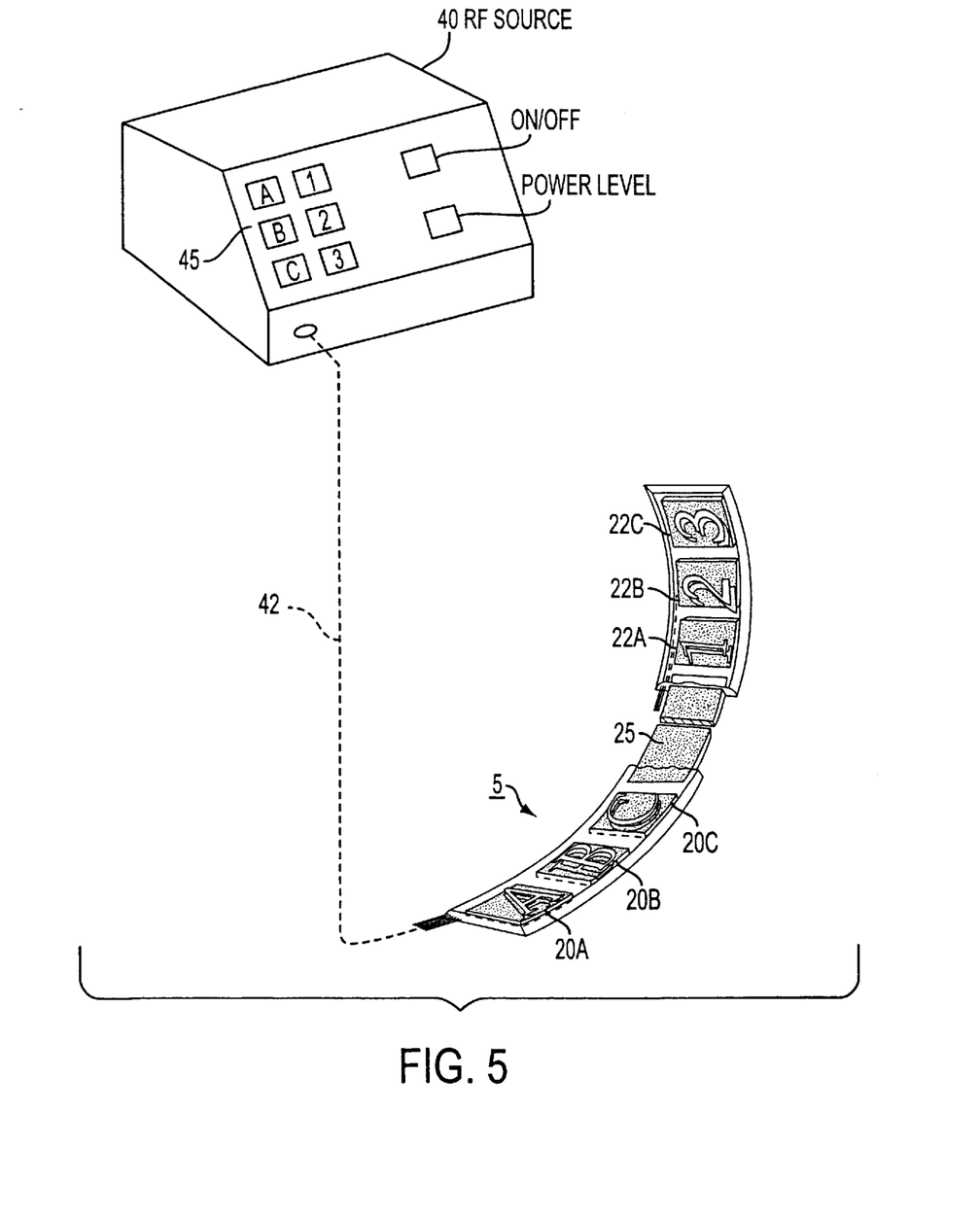
FIG. 5 is a schematic block diagram of a controller suitable for use with the present invention.

With respect to FIG. 5, RF source 40, adapted to deliver bi-polar RF current between selected paired bi-polar electrodes from groups 20 and 22, is described. Control panel 45 includes selectors A–C and 1–3, or alternatively, selector combinations A1, A2, A3, B1, B2, etc. (not shown) corresponding to the active electrodes or possible electrode pairings. The surgeon may, for example, press buttons on control panel 45 to direct bi-polar RF current flow to and between the selected bi-polar electrode pairing. The RF source 40, for example, may be any suitable electrosurgical RF generator capable of controlling energy delivery to the electrode array at low-power levels, for example, from about 0.5 to 25 watts.

Figure 6A:
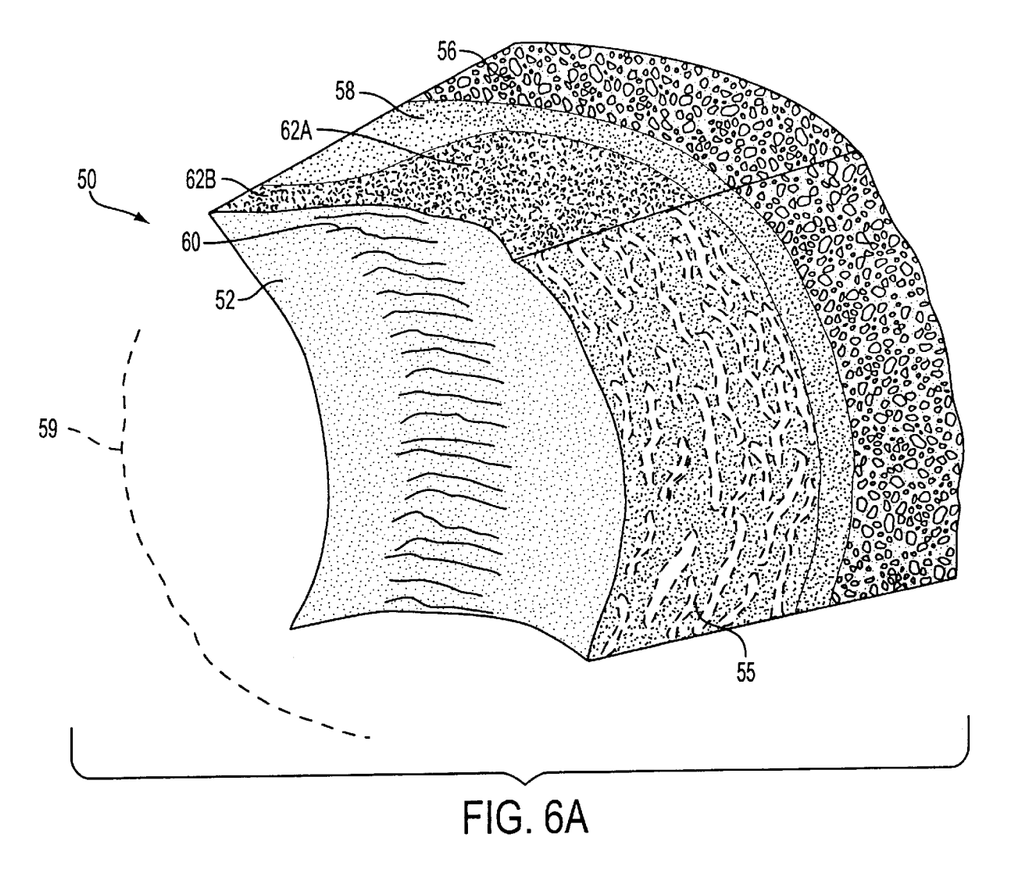
FIGS. 6A–6E depict a sequence of using the electrode array of FIG. 2 to perform "low rate" shrinkage of collagenous tissue of a glenohumeral joint to treat unidirectional joint instability.

Referring now to FIG. 6A, a schematic view of glenohumeral joint capsule 50 is shown with synovial surface 52 overlying collagen-containing ligament layer 55. The end of the scapula is called the glenoid, and is indicated at 56 having periosteum 58. The joint is partly stabilized by a ring of fibrous cartilage surrounding the glenoid called the labrum (indicated in phantom view at 59).

To access the capsule, the surgeon makes a standard posterior access portal for an endoscope. A standard anterior portal then is created at the upper border of the subscapular is tendon and through the rotator interval. A sleeve or cannula disposed through the anterior portal allows for introduction of electrode array 5 of the present invention. Generally, the joint capsule is prepared for standard arthroscopic fluid inflows and outflows, although such fluids are an optional aspect of the procedure described herein.

Figure 6B:
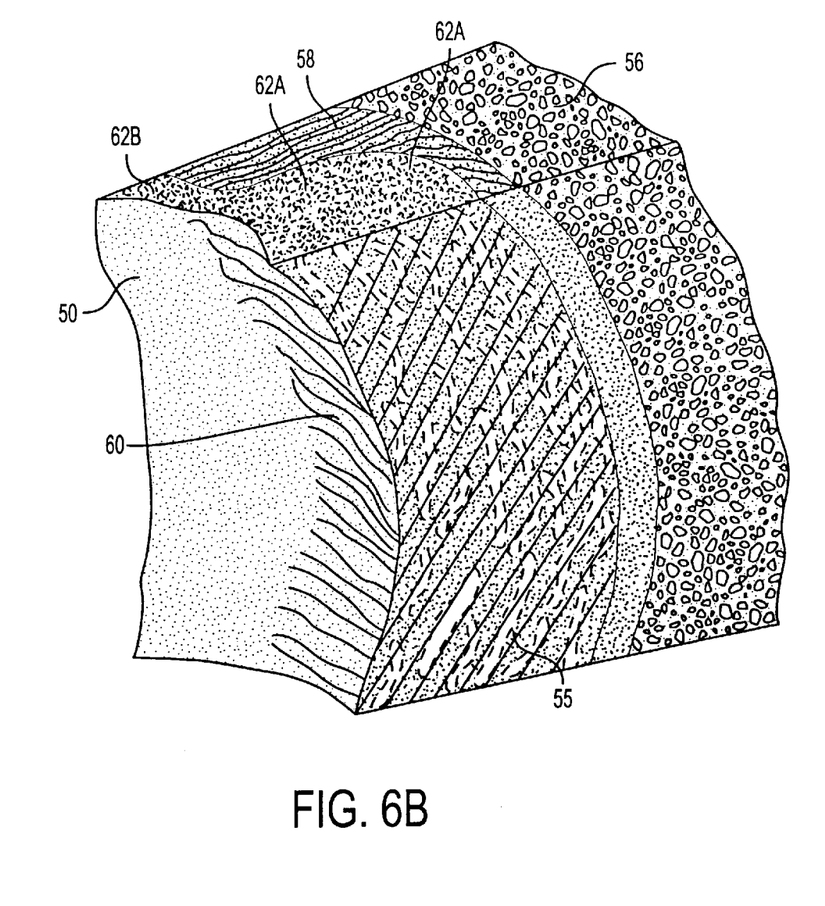

In FIG. 6A, the joint capsule (humeral head not shown) has lax ligament portions indicated at band 60, such as may be caused by an acute-event injury and result in a unidirectional instability. As shown in FIGS. 6A–6B, the collagen ligament complex varies in thickness within the joint capsule, e.g., with thick area 62A and thin area 62B (ligament thickness exaggerated for clarity). FIG. 6B shows in sectional view the depth of capsular ligaments targeted for collagen shrinkage, the area targeted for treatment extending from the synovial surface to the periosteum across the lax portion.

Figure 6C:
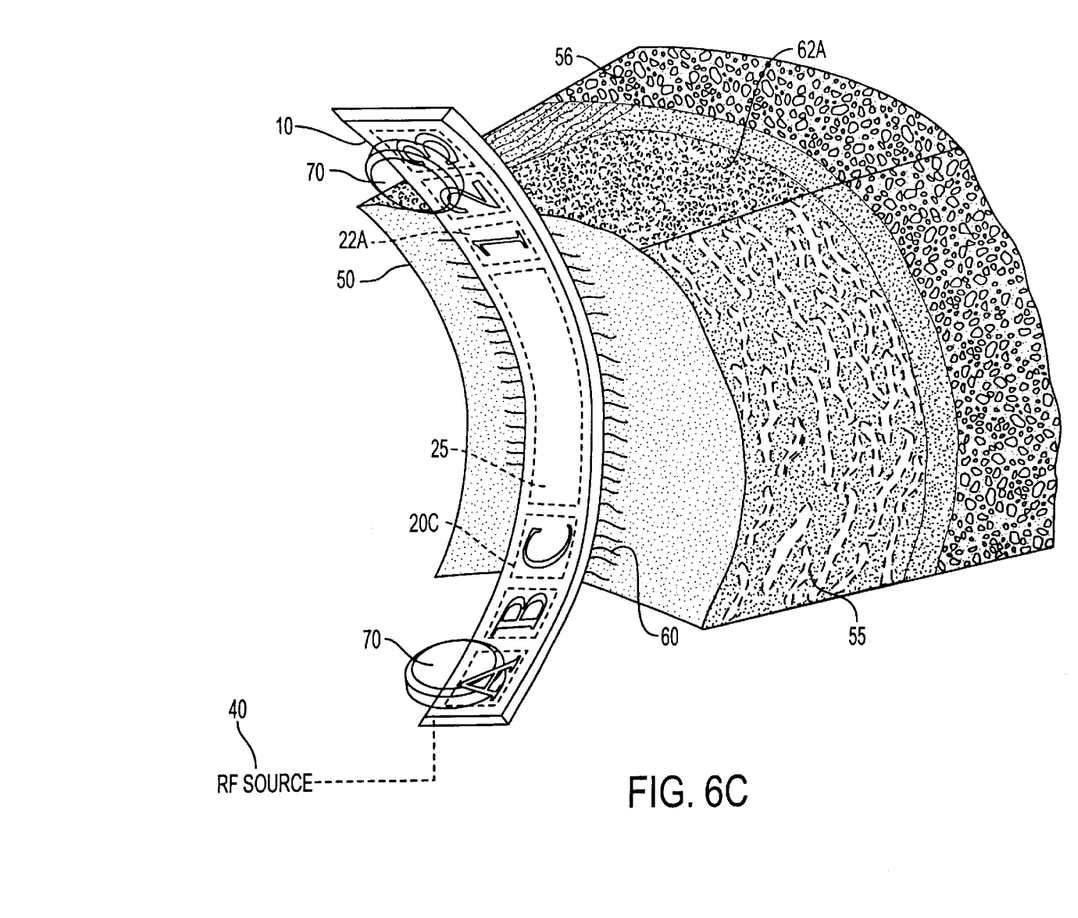

Now referring to FIG. 6C, the surgeon introduces electrode array 5 through a suitable portal or incision into joint capsule 50, so that power cord 42 extends out of the patient's body and may be connected to RF source 40. Electrode-array 5 may be introduced into the working space with a suitable instrument, e.g., a grasper, and its position is adjusted until surface 12 is positioned in contact with the capsular surface overlying the collagenous ligament tissue targeted for treatment, i.e., underlying band 60. When electrode array 5 is disposed in a suitable position, the surgeon may use sponges 70 (shown in phantom view) or other formable material to retain electrode array 5 in position relative to the humeral head (not shown) and the capsular surface.

The surgeon then identifies which pair of electrodes 20A–20C and 22A–22C best span band 60 of tissue targeted for treatment. For example, in FIG. 6C, electrode 20C (with overlying visual indicator mark "C") and electrode 22A (with overlying visual indicator mark "1") are best positioned in the joint capsule to deliver the desired thermal treatment. The surgeon accordingly selects the appropriate controls on the control panel 45 of RF source 40 for RF delivery to the selected pair of electrodes.

Figure 6D:
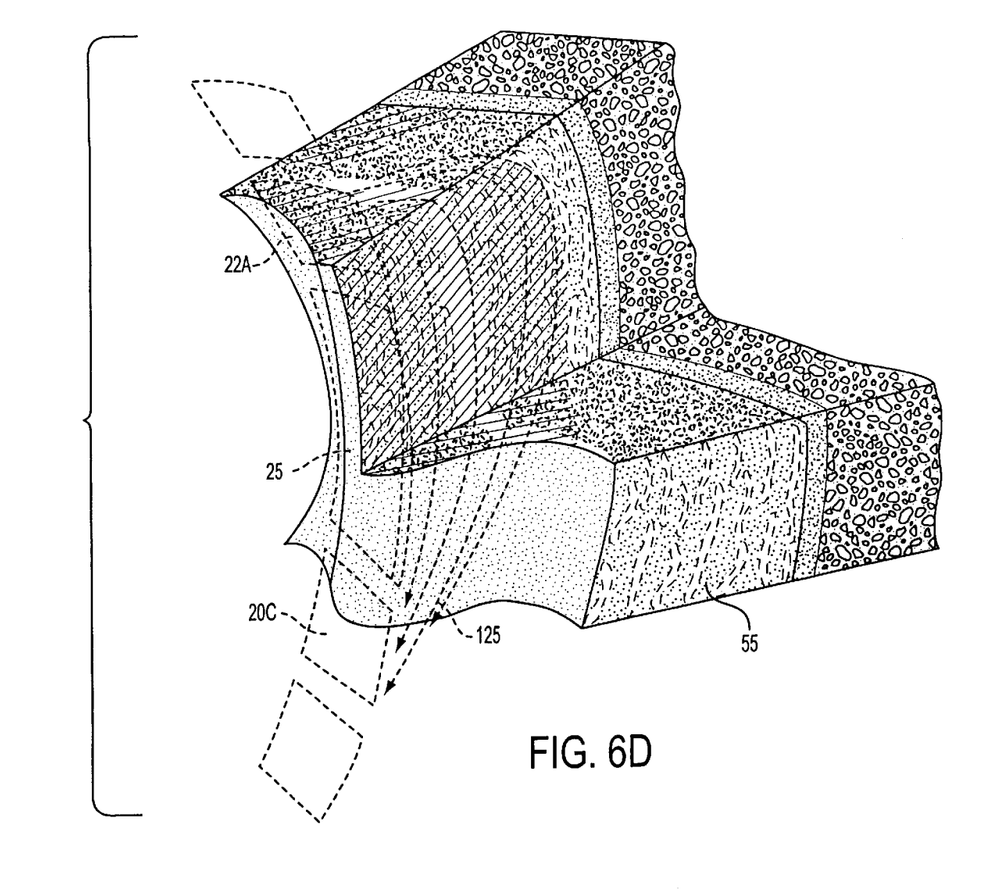

In FIG. 6D the joint capsule is shown with arrows 125 indicating the path of the RF current flowing between the selected pair of bi-polar electrodes. Of particular interest to the invention, RF energy flows between electrode 22A and electrode 20C and through the tissue in contact with intermediate channeling electrode 25. As indicated by arrows 125, the RF current generally flows through the collagenous tissue directly under channeling electrode 25 (in band 60) that is targeted for treatment along similar "directed paths" for the entire time the electrodes are activated. By contrast, in the previously known mono-polar RF delivery methods depicted in FIGS. 1, the current flow is in a constant state of flux.

It has been determined that the channeling electrode of the present invention generally confines the RF current path to the tissue region proximate to conductive element as indicated by arrows 125. This is highly desirable because stray RF current flow between the bipolar electrodes is largely eliminated, thereby providing higher current density (energy density) in the targeted tissue with lower RF power levels.

Moreover, the RF current travels generally parallel to channeling electrode 25, thereby heating the entire depth of collagen tissue and developing a fairly uniform thermal gradient from capsular surface 52 to periosteum 58. This aspect of the invention is to be contrasted with previously known mono-polar RF delivery, wherein the capsular surface receives excess heat (possibly ablating surface 52) and RF current flow between the probe and ground plate is perpendicular to the surface, or random.

Figure 6E:
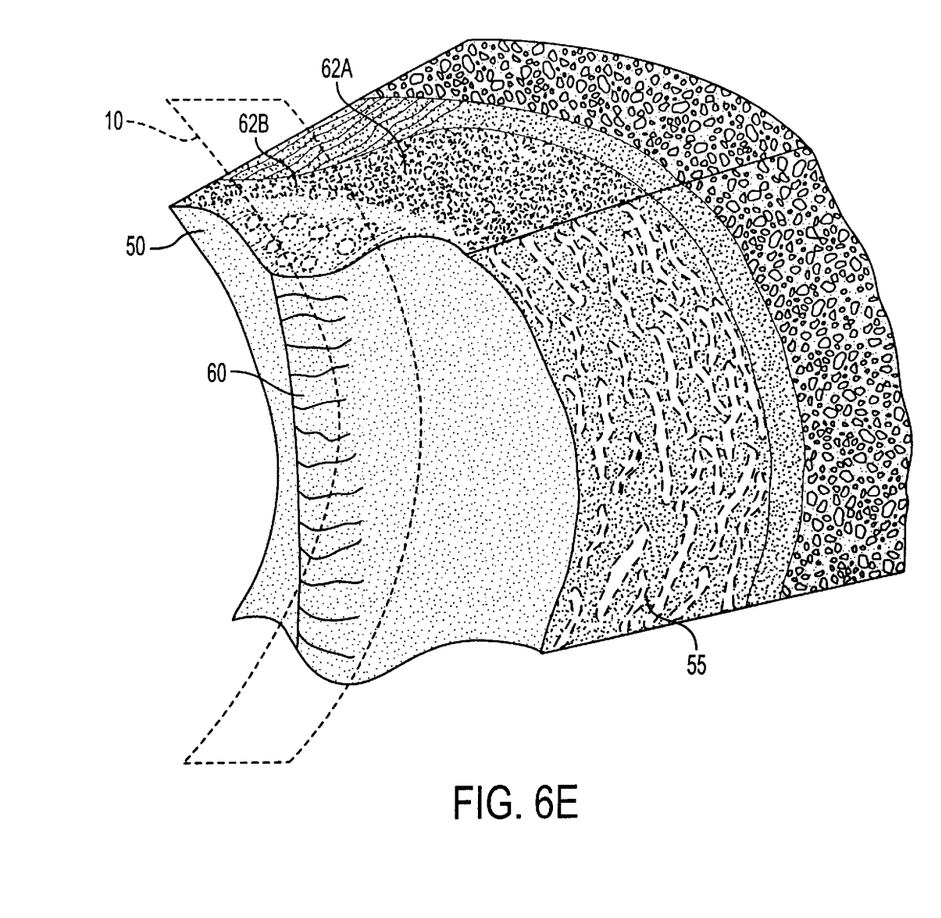

FIG. 6E shows the joint capsule after shrinking collagen in ligament 55 with the capsular surface shifted toward the humeral head (not shown) along band 60 (electrode array 5 is shown in phantom view and the extent of capsular shift is exaggerated for purposes of illustration). By thus directing RF current along the desired path along and below synovial surface 52, it been found that RF current intensity can be reduced significantly, when compared to previously known mono-polar devices and methods.

The method of the present invention thus utilizes a stationary electrode (rather than a painting technique), with the bi-polar electrodes and channeling electrode pressed against capsular surface 52. In a preferred method of the present invention, RF current is applied for times ranging between 5 seconds and 180 seconds at powers in a range of 0.5 to 25 watts, more preferably 2 to 20 watts, and still more preferably, 2 to 10 watts. The duration of RF current for low-rate collagen shrinkage more preferably ranges from 10 seconds to 120 seconds, and still more preferably, from 20 seconds to 60 seconds.

Compared to the rapid shrinkage of previously known systems (typically 1 to 2 seconds), the longer time intervals provided by the present invention allow "low-rate" collagen shrinkage, affording the surgeon sufficient time to evaluate the extent of capsular shrinkage and to terminate RF energy delivery based on observation. Using the apparatus and methods of the present invention, the surgeon simply may terminate the low-level RF power at any time during capsule shrinkage to gauge the correct amount of shrinkage. After shrinking targeted ligament tissue in the a first location, the surgeon then may move electrode array 5 to a second location.

It should be appreciated that applications of the electrode array of the present invention may be generalized to deliver controlled levels of radiofrequency energy to subsurface tissues at other locations in a body for a variety of therapeutic purposes, such as for bio-stimulation or bio-excitation purposes.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. Apparatus for delivering bi-polar RF current from an RF source to tissue in a medical procedure, the apparatus comprising:
   a substantially transparent elongated member having a first end, a second end, and an intermediate region disposed between the first and second ends, the elongated member comprising an electrically insulating material;
   a first electrode disposed on the first end, the first electrode adapted to be coupled to the RF source;
   a second electrode disposed on the second end, the second electrode adapted to be coupled to the RF source;
   a channeling electrode disposed in the intermediate region for contacting tissue, the channeling electrode spaced apart from, and electrically insulated from, the first and second electrodes, the channeling electrode comprising an electrically conductive material, wherein the channeling electrode is adapted to direct a path of the bi-polar RF current between the first electrode and the second electrode through tissue contacting the channeling electrode.

2. The apparatus of claim 1
   wherein the elongated member comprises a flexible material.

3. The apparatus of claim 1
   wherein the elongated member has a first surface, each one of the first, second and channeling electrodes having a surface exposed on the first surface.

4. The apparatus of claim 1 further comprising
   indicator marks that assist in visualizing the location of the first and second electrodes.

5. The apparatus of claim 1
   wherein the first and second electrodes are adapted to delivery RF energy to tissue in a range from about 0.5 to 25 watts.

6. Apparatus for delivering bi-polar RF current from an RF source to tissue in a medical procedure, the apparatus comprising:
   a substantially transparent elongated member having a first end, a second end, and an intermediate region disposed between the first and second ends, the elongated member comprising an electrically insulating material;
   a plurality of first electrodes disposed on the first end, each one of the plurality of first electrodes adapted to be coupled to the RF source;
   a plurality of second electrodes disposed on the second end, each one of the plurality of second electrodes adapted to be coupled to the RF source;
   a channeling electrode disposed in the intermediate region for contacting tissue, the channeling electrode spaced apart from, and electrically insulated from, the pluralities of first and second electrodes, the channeling electrode comprising an electrically conductive material, wherein the channeling electrode is adapted to direct a path of the bi-polar RF current between a selected one of the plurality of first electrodes and a selected one of the plurality of second electrodes through tissue contacting the channeling electrode.

7. The apparatus of claim 6
   wherein the elongated member comprises a flexible material.

8. The apparatus of claim 6
   wherein the elongated member has a first surface, each one of the pluralities of first and second electrodes and the channeling electrode having a surface exposed on the first surface.

9. The apparatus of claim 6 further comprising
   indicator marks that assist in visualizing the location of the pluralities of first and second electrodes.

10. The apparatus of claim 6
    wherein the selected ones of the pluralities of first and second electrodes are adapted to delivery RF energy to tissue in a range from about 0.5 to 25 watts.

11. The apparatus of claim 6 further comprising
    means for determining the selected ones of the pluralities of first and second electrodes.

* * * * *